United States Patent [19]

Misaki et al.

[11] 4,385,112

[45] May 24, 1983

[54] NUCLEOSIDE OXIDASE AND PROCESS FOR MAKING SAME, AND PROCESS AND KIT FOR USING SAME

[75] Inventors: Hideo Misaki, Shizuoka; Shigeru Ikuta, Kanazawa; Kazuo Matsuura, Shizuoka, all of Japan

[73] Assignee: Toyo Jozo Kabushiki Kaisha, Shizuoka, Japan

[21] Appl. No.: 292,154

[22] Filed: Aug. 12, 1981

[30] Foreign Application Priority Data

Aug. 12, 1980 [JP] Japan ................................. 55-110762
Oct. 14, 1980 [JP] Japan ................................. 55-144064
Oct. 30, 1980 [JP] Japan ................................. 55-152627

[51] Int. Cl.$^3$ .......................... C12N 9/06; C12P 7/40; C12P 13/00; C12Q 1/26; C12Q 1/28; C12Q 1/34; C12Q 1/42; C12Q 1/68; C12R 1/40
[52] U.S. Cl. ......................................... 435/6; 435/15; 435/18; 435/25; 435/21; 435/28; 435/191; 435/810; 435/877; 435/136; 435/128
[58] Field of Search ................... 435/6, 15, 18, 25, 26, 435/28, 136, 191, 810, 877, 21, 4, 128

[56] References Cited

FOREIGN PATENT DOCUMENTS 2488618  2/1982  France ................................. 435/25

OTHER PUBLICATIONS

Liu et al., Biochemistry, 11(11), 2172–2176 (1972).

*Primary Examiner*—Esther M. Kepplinger
*Attorney, Agent, or Firm*—Young & Thompson

[57] ABSTRACT

A microorganism strain B-0781 belonging to the genus Pseudomonas isolated from a soil sample from an onion field in Japan, produces a novel enzyme nucleoside oxidase having substrate specificity on various nucleosides and enzyme action to catalyze enzymatic reactions involving various nucleosides. The novel nucleoside oxidase is produced by culturing a nucleoside-oxidase-producing microorganism belonging to the genus Pseudomonas in a nutrient medium containing assimilable carbon and nitrogen and inorganic salt, and isolating the thus-formed nucleoside oxidase from the cultured cells. Various nucleoside-5'-carboxylic acids can be produced, by incubating the novel nucleoside oxidase with a nucleoside having a 5'-hydroxymethyl group, in an aqueous medium under aerobic conditions, and isolating the thus-formed nucleoside-5'-carboxylic acid from the incubation medium. Assay methods for nucleosides in liquid samples are provided, which comprise incubating the sample with nucleoside oxidase, thereby consuming oxygen and generating hydrogen peroxide and nucleoside-5'-carboxylic acid by acting on nucleoside, and quantitatively determining consumed oxygen or liberated hydrogen peroxide. A kit for nucleoside assay is provided, which contains the recited ingredients.

15 Claims, 17 Drawing Figures

2'-DEOXYADENOSINE (mM)

ARABINOSYLADENINE (mM)

NUCLEOSIDE OXIDASE AND PROCESS FOR MAKING SAME, AND PROCESS AND KIT FOR USING SAME

This invention relates to a novel nucleoside oxidase and to a process for its production, a process for the production of nucleoside-5′-carboxylic acid based on the substrate specificity and enzymatic action of the novel nucleoside oxidase, a novel assay method for nucleoside using the novel nucleoside oxidase, and a kit for the assay of nucleoside in a sample.

We have found that a microorganism strain B-0781 belonging to the genus Pseudomonas isolated from a soil sample from an onion field in Ono-shi, Hyogo-ken, Japan, produced in its bacterial cells a novel enzyme (nucleoside oxidase) having the following biochemical properties:

Substrate specificity: at least having substrate specificity on a nucleoside or its derivative of the formula [I], [Ib] or [Ic],

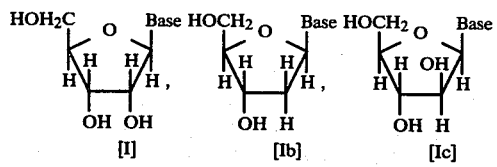

wherein Base means a nucleic acid base residue or its derivative.

Enzymatic action: at least having catalytic activity on the following enzymatic reactions of the equations [II], [III], [IV], [V], [VI] and/or [VII]; for substrate [I]:

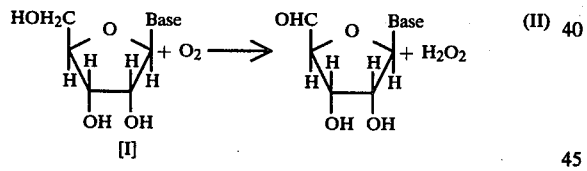

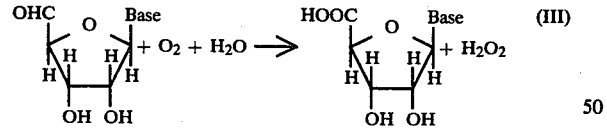

for substrate [Ib]:

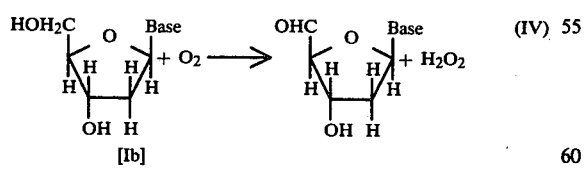

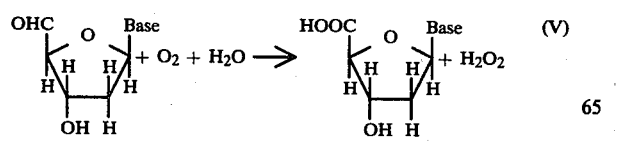

for substrate [Ic]:

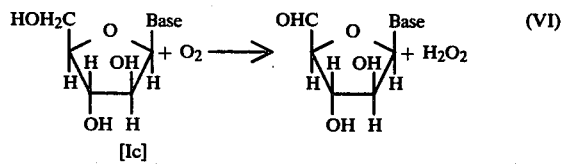

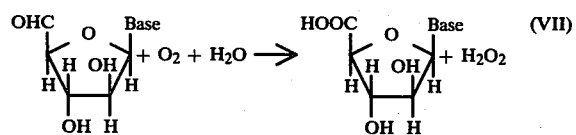

The novel enzyme catalyzes an oxidative reaction at the sugar moiety in nucleoside as a substrate, while consuming oxygen and generating hydrogen peroxide, and the said enzyme has been designated as nucleoside oxidase.

The substrate specificity, enzymatic action and assay method are as follows:

(1) Substrate specificity

Relative enzymatic activities on various substrates (nucleoside, nucleic acid base, sugar, and nucleotide, each 1 mM concentration) shown in Table 1 were measured. As shown in Table 1, the enzyme of the present invention reacts on a sugar moiety and does not react on a nucleic acid base or single sugar. Also the enzyme reacts on a nucleoside having ribose, deoxyribose or arabinose as a sugar moiety and the reaction does not depend on the kind of base moiety of the nucleoside. No reaction on nucleotide is observed.

Therefore, the enzyme of the present invention has substrate specificity at least on the nucleoside or its derivative shown in formula [I], [Ib] or [Ic].

TABLE 1

| | Substrate | Relative activity (%) |
|---|---|---|
| Nucleoside | adenosine | 100 |
| | guanosine | 97.1 |
| | thymidine | 94.3 |
| | cytidine | 65.7 |
| | inosine | 91.4 |
| | xanthosine | 14.3 |
| | uridine | 94.3 |
| | arabinosylcytosine (1-β-D-arabinofuranosylcytosine) | 8.1 |
| | arabinosyladenine (1-β-D-arabinofuranosyladenine) | 67.2 |
| | 2′-deoxyadenosine | 99.1 |
| | bredinine* | 48.2 |
| Nucleic acid base | adenine | 0 |
| | thymine | 0 |
| | xanthine | 0 |
| | uracil | 0 |
| | hypoxanthine | 0 |
| Sugar | D-ribose | 0 |
| | α-D-ribose-1-phosphate | 0 |
| Nucleotide | 5′-AMP | 0 |
| | 5′-GMP | 0 |
| | 5′-CMP | 0 |
| | 5′-IMP | 0 |
| | 5′-XMP | 0 |
| | 5′-UMP | 0 |
| | 5′-ADP | 0 |
| | 5′-ATP | 0 |
| | mixture of adenine and D-ribose | 0 |

*4-carbamoyl-1-β-D-ribofuranosylimidazolium-5-olate (2) Enzymatic action:

(A) Identification of reaction product:

A reaction mixture (100 ml) consisting of 0.2 M dimethylglutarate-NaOH buffer (pH 6.0) 10 ml, adenosine 500 mg, nucleoside oxidase 180 U, catalase 15,000 U and distilled water 90 ml, is stirred with aeration at pH 6. During the reaction process, the pH decreased, which shows the formation of an acidic substance. After 90 minutes at 37° C., the pH was adjusted to pH 2.0 by adding HCl. A precipitated substance was collected by centrifugation and washed with aqueous HCl (pH 3). The washed material was dissolved by adding 1 N-NaOH to adjust to pH 8.5. Further HCl was added to adjust to pH 3 and insoluble material was collected. Elemental analysis: C=42.62%, H=3.93%, N=24.9% and O=28.55%. Molecular weight: 281. Molecular formula: $C_{10}H_{11}N_5O_5$. Infrared spectrum and UV spectrum were identical with authentic adenosine-5'-carboxylic acid.

(B) Thin layer chromatogram of reaction product during reaction:

A reaction mixture consisting of 0.2 M dimethylglutarate-NaOH buffer (pH 6.0) 10 ml, 10 mM adenosine 5 ml, nucleoside oxidase 20 U, catalase 1000 U and distilled water 45 ml was incubated at 37° C. Reaction mixture samples were collected at 0, 5, 10, 20 and 60 minutes. Each sample was heated at 100° C. for 2 minutes and subjected to ultrafiltration. TLC: silica gel plate. Developer: acetonitrile: 0.1% aqueous ammonium chloride=7:3. Standard authentic sample:

adenosine (abbreviated as Ad)

adenosine-5'-carboxylic acid (Ad-A).

As shown in FIG. 1, a spot corresponding to a compound oxidized at the 5'-hydroxymethyl group of adenosine to an aldehyde group was confirmed. Further reaction resulted in oxidation to the 5'-carboxyl group and adenosine-5'-carboxylic acid was confirmed as the final product.

(C) Amount of oxygen consumption and hydrogen peroxide generation in the reaction:

Nucleoside oxidase (3 U.) was added to the reaction mixture (1.0 ml) consisting of 0.2 M dimethylglutarate-NaOH buffer (pH 6.0) 0.4 ml, 0.2% N,N-diethyl-m-toluidine 0.1 ml, 0.3% 4-aminoantipyrine 0.1 ml, peroxidase (50 U/ml) 0.1 ml, 1.0 mM adenosine 0.05 ml and distilled water 0.25 ml. The amount of consumed oxygen (measured by an oxygen electrode) and generated hydrogen peroxide (colorimetric assay at 545 nm) were measured. Results: adenosine 0.05$\mu$ mole; consumed oxygen 0.097$\mu$ mole; and generated hydrogen peroxide 0.101$\mu$ mole. This result suggested that 1 mole of adenosine consumes 2 moles of oxygen and generates 2 moles of hydrogen peroxide.

(D) Ammonia formation:

No ammonia formation was observed in this reaction.

As hereinabove explained, the enzyme of the present invention catalyzes a reaction from adenosine to adenosine-5'-carboxylic acid through adenosine-5'-aldehyde.

The reaction schema is shown as follows:

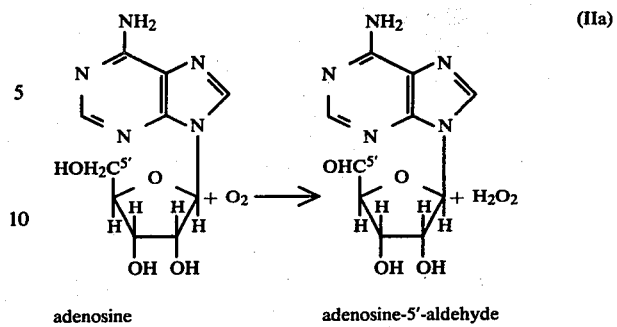

adenosine       adenosine-5'-aldehyde

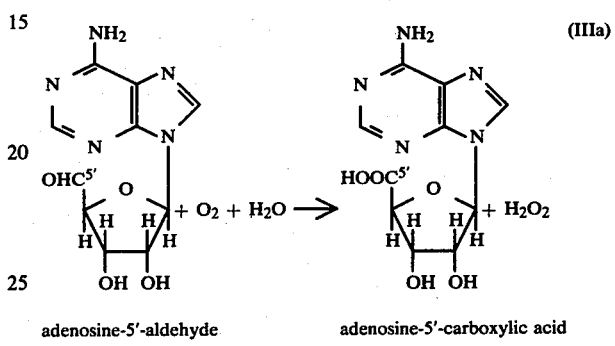

adenosine-5'-aldehyde       adenosine-5'-carboxylic acid

The enzyme of the present invention has substrate specificity on various nucleosides in Table 1 and formulas [I], [Ib] and [Ic]. The enzyme also catalyzes at least one reaction [II], [III], [IV], [V], [VI] and/or [VII]. Therefore, the enzyme is a novel enzyme which has prior unknown enzymatic action and substrate specificity.

The enzymatic reaction can also be represented as the following general schemata [VIII], [IX] and [X]:

for substrate [I]       (VIII)

for substrate [Ib]       (IX)

for substrate [Ic]       (X)

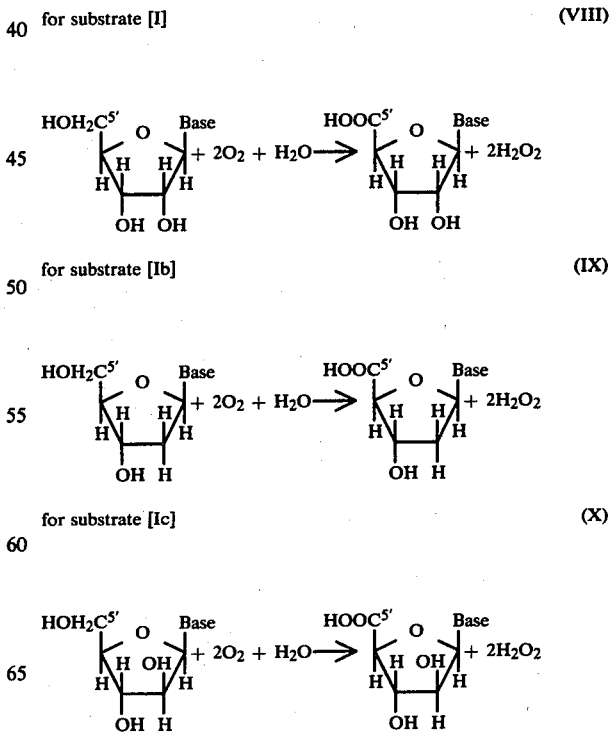

wherein Base is a nucleic acid base or its derivative.

(3) Assay method

A reaction mixture (0.5 ml) consisting of 0.2 M dimethylglutarate-NaOH buffer (pH 6.0) 0.2 ml, 0.2 w/w% N,N-diethyl-m-toluidine 0.05 ml, 0.3 w/w% 4-aminoantipyrine 0.05 ml, 10 mM adenosine 0.05 ml and distilled water 0.10 ml was pre-incubated at 37° C. for 3 minutes. After adding enzyme solution (20 μl), the mixture was incubated at 37° C. for 10 minutes, and 0.5 ml of 4 M urea solution containing 0.2% cetylpyridiniumchloride was added to stop the reaction. Optical density at 545 nm in a 1.0 cm cell was measured within 5 minutes after adding 2.0 ml of distilled water (As). Then the enzyme solution was replaced by distilled water (20 μl) as a control ($A_B$).

The difference ($A_S - A_B$) of optical density between enzyme solution (As) and control ($A_B$) shows the enzyme activity. Enzymatic activity should be measured within the value of As below 0.15.

One unit (1 U.) of enzyme activity is that amount of enzyme such that 1μ mole of hydrogen peroxide is generated in one minute at 37° C. with adenosine as substrate, and represented by the following equation:

Enzyme activity (U/ml)=1.25×($A_s - A_B$)×dilution ratio.

The novel enzyme of the present invention has the following physico-chemical and biochemical properties:

Km value: $4.5 \times 10^{-5}$ M (for adenosine);
Isoelectric point: pH 4.7 (electrophoresis using as a carrier ampholite);
Molecular weight: about 240,000 (gel-filtration method using Sepharose CL-6B (trademark));
Optimum pH: shown in FIG. 2; pH 5–6 measured by glycine-HCl buffer. In the figure,
  o-o: glycine-HCl buffer (40 mM),
  ●-●: dimethylglutarate-NaOH buffer (40 mM),
  ∆-∆: phosphate buffer (40 mM). Oxygen consumption was measured by oxygen electrode.
Optimum temperature: 45°–55° C. as shown in FIG. 3. Remaining activity at various temperatures was measured by the assay method.
Heat stability: stable at 60° C. for 10 minutes as shown in FIG. 4. Enzyme activity was assayed after 10 minutes incubation in a phosphate buffer (pH 6.0, 40 mM).
pH stability: pH 4–9 as shown in FIG. 5,
  o-o: Britton-Robinson buffer (150 mM),
  ●-●: dimethylglutarate-NaOH buffer (150 mM),
  ∆-∆: phosphate buffer (150 mM),
  ▲-▲: tris-HCl buffer (150 mM).
After incubation for 60 minutes at 37° C., the reaction mixture was diluted to 40 times dilution and 20 μl was used for assay.

TABLE 2

| metal ions | relative activity (%) |
|---|---|
| control | 100 |
| $Mg^{2+}$ | 104 |
| $Ba^{2+}$ | 100 |
| $Ca^{2+}$ | 102 |
| $Mn^{2+}$ | 110 |
| $Zn^{2+}$ | 94 |
| $Co^{2+}$ | 104 |
| EDTA | 98 |

TABLE 2-continued

| metal ions | relative activity (%) |
|---|---|
| PCMB | 102 |

TABLE 3

Effect of surface active agent: Table 3.

| | | Relative activity (%) |
|---|---|---|
| None | | 100 |
| 0.1 w/w % | Triton X-100% | 104 |
| 0.1 w/w % | Bridge 35% | 100 |
| 0.1 w/w % | sodium dodecyl sulfate | 66 |
| 0.1 w/w % | sodium lauryl benzene sulfonate | 38 |
| 0.1 w/w % | sodium deoxycholate | 102 |
| 0.1 w/w % | Cation FB-500% | 70 |
| 0.1 w/w % | Cation DT-202% | 60 |
| 0.1 w/w % | cetyl trimethylammonium chloride | 78 |

*trademark

The bacterial strain B-0781 has the following toxonomical properties:

A. Macroscopic observation

30° C. for 18–24 hours cultivation:
(1) Nutrient gar slant:
Growth linearly, pale yellowish gray to grayish white.
No soluble pigment formation.
(2) Nutrient agar plate:
Round hilly colonies with smooth edge, semi-fluorescent, pale yellowish gray to grayish white. No formation of soluble pigment.
(3) Liquid culture:
Settles from turbid solution. Thin pellicles formed but easily destroyed by gentle shaking.
(4) Gelatin polylayer medium:
Growth along stab line. No gelatin hydrolysis.
(5) BCP milk medium:
Weak alkali. No peptonization.
(6) Anaerobic growth:
No growth.

B. Microscopic observation

Straight or slightly curved rods and cocci. Single or double pairs or short chains. Motile with polar flagellae. 0.5×0.1–1.5μ. No spore formation. No polymorphism.

C. Physiological and biochemical properties

| (1) Gram stain: | — |
|---|---|
| (2) Acid fast stain: | — |
| (3) OF test | 0 (oxidative decomposition) |
| (4) Catalase formation: | + |
| (5) Oxidase formation: | + |
| (6) Urease formation: | |
|   SSR medium (Stuart, van Stratum & Rustigian medium): | — |
|   Christenssen medium: | + |
| (7) Gelatin hydrolysis: | — |
| (8) Starch hydrolysis: | — |
| (9) Casein hydrolysis: | — |
| (10) Esculin hydrolysis: | — |
| (11) Cellulose hydrolysis: | — |
| (12) Arginine hydrolysis: | + |
| (13) Poly-β-hydroxybutyrate accumulation: | — |
| (14) Indole formation: | — |
| (15) $H_2S$ formation: | + |
| (16) Acetoin formation: | — |

-continued

| | |
|---|---|
| (17) Nitrate reduction: | — |
| (18) Denitrification reaction: | — |
| (19) Utilization of citrate: | + |
| (20) GC content of DNA: | 59% |
| (21) Acid formation from sugar: | |

| Sugar | Acid | Gas |
|---|---|---|
| adnitol | — | — |
| L(+) arabinose | (+) | — |
| cellobiose | (+) | — |
| dulcitol | — | — |
| meso-erythritol | — | — |
| fructose | — | — |
| fucose | + | — |
| galactose | + | — |
| glucose | + | — |
| glycerin | — | — |
| inositol | — | — |
| inulin | — | — |
| lactose | (+) | — |
| maltose | — | — |
| mannitol | — | — |
| mannose | + | — |
| meleditose | — | — |
| melibiose | + | — |
| raffinose | — | — |
| L(+) rhamnose | (+) | — |
| salicin | — | — |
| L(−) sorbose | — | — |
| sorbitol | — | — |
| starch | — | — |
| sucrose | — | — |
| trehalose | — | — |
| xylose | + | — |

| | |
|---|---|
| (22) Growth pH: pH 4.5–9.0 | |
| (23) Growth temperature: 10–37° C. | |
| (24) Utilization of ammonia nitrogen: | + |
| (25) Utilization of nitrate nitrogen: | + |

The taxonomical properties of the strain B-0781 were compared by consulting "Bergey's Manual of Determinative Bacteriology", 8th Ed., 1974 and "Identification of Medical Bacteriology", 1974.

The strain B-0781 was determined to belong Pseudomonas on the basis of Gram negative, positive catalase and oxidase formation, oxidative decomposition of glucose, motility by polar flagella cocci and good growth on pH 7.0 nutrient agar (slant). Further detailed comparison reveals that the strain B-0781 was identical with Pseudomonas putida.

| | Strain B-0781 | Pseudomonas putida |
|---|---|---|
| catalase.oxidase formation | + | + |
| fluorescent pigment formation (King B medium) | + | + |
| gelatin-starch-casein hydrolysis | — | — |
| arginine decomposition | + | + |
| poly-β-hydroxybutyrate accumulation | — | — |
| indole acetoin formation | — | — |
| nitrate reduction | — | d |
| citrate utilization | + | + |
| galactose (acid) | + | + |
| glucose (acid) | + | + |
| mannose (acid) | + | + |
| xylose (acid) | + | + |
| L(+) arabinose (acid) | (+) | d |
| fructose (acid) | — | d |
| glycerin (acid) | — | — |
| inositol (acid) | — | d |
| lactose | (+) | — |
| mannitol | + | — or (d) |
| salicine | — | (d) |
| sucrose | — | — |
| maltose | — | (d) |
| GC content of DNA | 59% | 60–63% | d: different

According to the above taxonomical data the strain B-0781 is referred to Pseudomonas putida B-0781 and has been deposited in the Fermentation Institute, Agency of Industrial Technology and Science, M.I.T.I., Japan as permanent culture collection FERM-P No. 5664.

An object of the present invention is to provide a novel enzyme nucleoside oxidase which at least has substrate specificity on a nucleoside of the formula [I], and catalyzes the reactions [II] and/or [III].

Another object of the present invention is to provide a process for the production of nucleoside oxidase, comprising culturing a nucleoside-oxidase-producing microorganism belonging to genus Pseudomonas in a nutrient medium, and isolating nucleoside oxidase thus produced from the cultured cells.

A further object of the present invention is to provide an assay method for nucleoside in a sample by measuring consumed oxygen or generated hydrogen peroxide.

A still further object of the present invention is to provide a process for the preparation of nucleoside-5'-carboxylic acid.

Yet another object of the present invention is to provide a kit for assaying nucleoside.

Other objects, features and advantages of the present invention will become apparent from a consideration of the following description, taken in connection with the accompanying drawings, in which.

Figure 1:
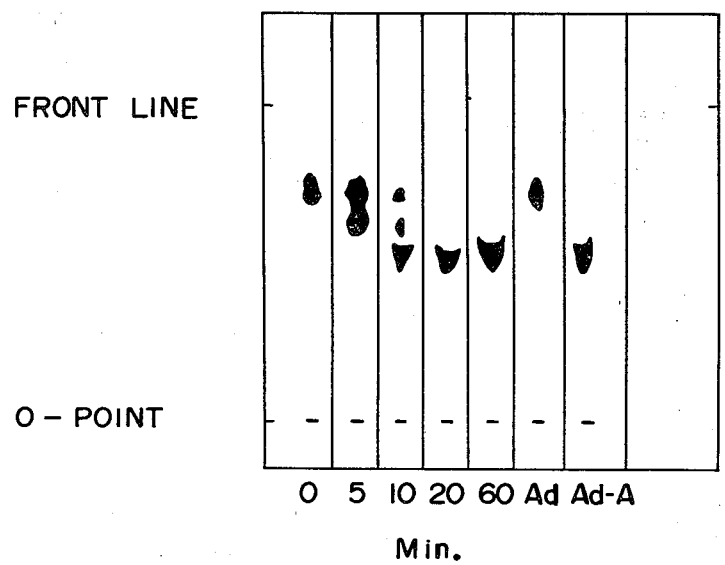
FIG. 1 is a thin layer chromatogram of the reaction product of the present invention during reaction.
Figure 2:
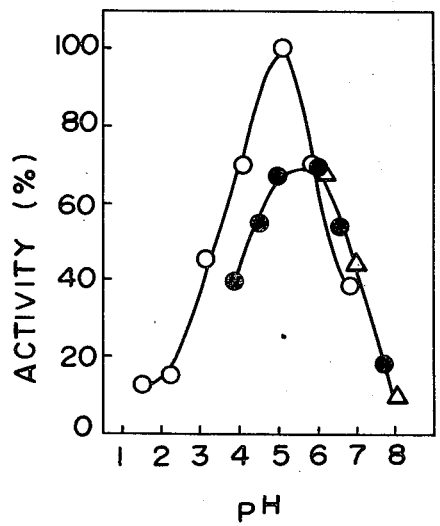
FIGS. 2–5 are graphs of optimum pH, optimum temperature, heat stability and pH stability, respectively, of the novel enzyme of the present invention.
Figure 3:
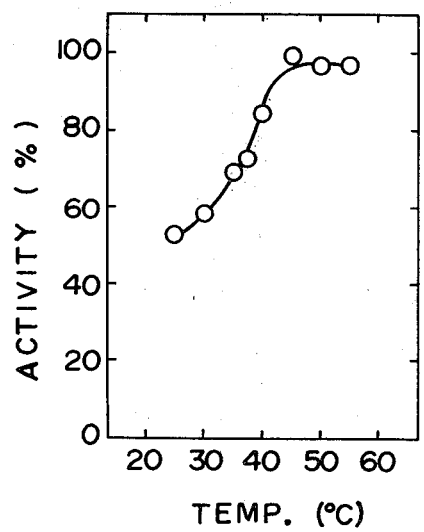
Figure 4:
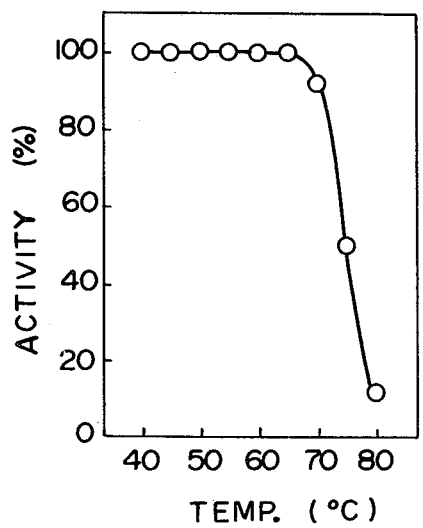
Figure 5:
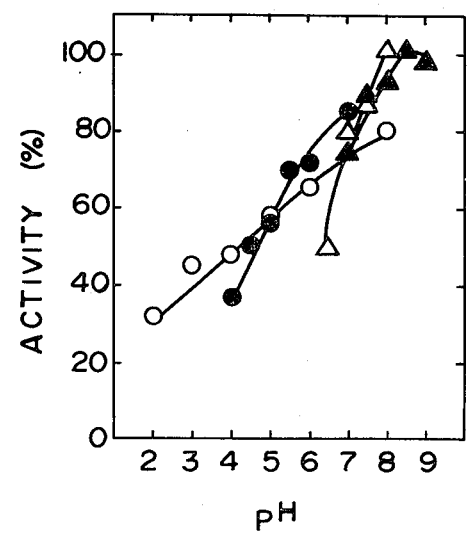

Nucleoside oxidase of the present invention is an enzyme having at least the substrate specificity and enzyme action hereinbefore explained and includes similar enzymes in which slight differences such as in molecular weight, Km value, effect of metal ions and surface active agents, have been observed.

As hereinabove explained, nucleoside-5'-carboxylate can be formed by the action of nucleoside oxidase of the present invention on nucleosides under aerobic conditions in an aqueous medium.

Furthermore, since the enzyme of the present invention acts on the 5'-hydroxymethyl group of the nucleoside in the sample on the basis of enzymatic action and substrate specificity, determination of nucleosides or enzymatic activity in nucleoside systems can be effected by measuring the amount of consumed oxygen or generated hydrogen peroxide.

The microorganism of the present invention is not limited to *Pseudomonas putida* hereinbefore described, and therefore other nucleoside-oxidase-producing microorganisms belonging to the genus Pseudomonas can be used. Natural and artificial mutants of the said microorganism can be used. Genetic engineering techniques applicable to nucleoside oxidase production such as transformation of corresponding genes of the present strain to other cells may also be applied and the nucleoside oxidase produced by these techniques is of course included in the present invention.

For production, a nucleoside-oxidase-producing microorganism belonging to the genus Pseudomonas is cultured in a conventional medium for enzyme production. Liquid or solid culture can be used. Submerged aeration culture is preferable for industrial production.

A conventional nutrient medium can be used. Assimilable nitrogen sources such as corn steep liquor, meat extract, soybean powder, casein, peptone, yeast extract, ammonium sulfate or ammonium chloride can be used. Assimilable carbon sources such as higher fatty acids, molasses, glucose or starch hydrolysate can be used. Inorganic salts such as NaCl, KCl, magnesium sulfate, potassium hydrogen phosphate or potassium dihydrogen phosphate can also be added to the culture medium if required. The production of nucleoside oxidase can be improved by adding 0.5–1% of a higher fatty acid such as oleic acid or palmitic acid.

Culturing temperature may vary depending on the desired rate of growth of the microorganisms and is preferably at 25°–35° C. Culturing time can be selected as desired, and is 15–50 hours. Culturing may be terminated when the highest concentration of nucleoside oxidase is present in the medium.

Nucleoside oxidase is accumulated in the cells of the microorganisms.

Extraction of the produced enzyme from these cells can be effected as follows:

Cultured cells are collected and the wet cells obtained are suspended in phosphate buffer or Tris-HCl buffer, which are treated by conventional cell decomposition techniques such as lysozyme treatment, sonication or French press treatment to obtain a crude nucleoside oxidase solution.

The crude enzyme solution can be purified by conventional purification methods for proteins. For example, a liquid containing enzyme is subjected to acetone, methanol, ethanol or isopropanol sedimentation, or salting out by salts such as ammonium sulfate, NaCl or aluminum sulate to precipitate the enzyme. The thus-obtained powder is purified until it shows electrophoretically a single band. For example, the sedimented enzyme is suspended in phosphate buffer, and chromatographed by using an ion exchanger such as diethylaminoethyl dextran gel, diethylaminoethyl cellulose or triethylaminoethyl dextran gel, and gel filtration such as with dextran gel or polyacrylamide. A purified powder of the enzyme can be obtained by lyophilization.

Nucleoside-5'-carboxylic acid can be prepared by reacting nucleosides with nucleoside oxidase in crude or purified form. The enzyme can be used in the form of a solution or in immobilized form. Examples of nucleosides are nucleosides or derivatives thereof having a 5'-hydroxymethyl group, such as adenosine, guanosine, thymidine, inosine, xanthosine, uridine, arabinosylcytosine, arabinosyladenine, 2'-deoxyadenosine or 2'-deoxyguanosine.

The aqueous medium for reaction is a medium having a stable pH range for nucleoside oxidase, for example an aqueous medium of pH 6–9, buffered with a dimethylglutarate-NaOH buffer, phosphate buffer or Tris-HCl buffer.

Aerobic conditions can be achieved by dissolving oxygen in an aqueous medium or by pre-aeration with air or oxygen in the medium.

Since two moles of oxygen per one mole of nucleoside having a 5'-hydroxymethyl group are required, aerobic conditions should be maintained, with a molar excess of oxygen.

The incubation temperature should be a stable temperature for the enzyme and naturally can be room temperature.

The amount and concentration of nucleoside oxidase or nucleosides having a 5'-hydroxymethyl group are not limited. Incubation time depends on the amount and concentration of the enzyme or substrates and other reaction conditions, and is preferably more than 20 minutes. The completeness of the reaction is determined by checking the remaining substrates or produced nucleoside-5'-carboxylic acids in a sample, using thin layer chromatography techniques.

In the reaction, hydrogen peroxide is formed and catalase is preferably first added to the reaction medium to convert hydrogen peroxide to water and free oxygen.

The isolation of the produced nucleoside-5'-carboxylic acid from the reaction mixture can be effected by adding aqueous hydrogen chloride or sulfuric acid by adjusting to pH 2–3 to precipitate the nucleoside-5'-carboxylic acid. For further purification, adsorption chromatography on an ion exchanger or recrystallization can be used.

By these methods, nucleoside-5'-carboxylic acids can be prepared from various nucleosides having a 5'-hydroxymethyl group.

The use of the nucleoside oxidase of the present invention on the basis of its substrate specificity and enzyme action for novel assay methods and a kit for assay of nucleosides will be described below.

Samples to be analyzed contain at least one nucleoside having a 5'-hydroxymethyl group, of the formula

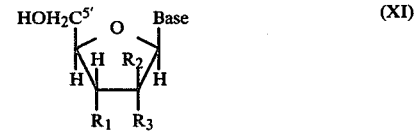 (XI)

wherein $R_1$, $R_2$ and $R_3$ are hydrogen or hydroxy and Base has the same meaning hereinbefore.

Examples of sample are as follows: a reagent sample containing nucleosides hereinbefore mentioned; sample for assaying activity of ribonuclease or deoxyribonuclease in which RNA, DNA or its oligonucleotide is hydrolyzed by corresponding hydrolases such as ribonuclease or deoxyribonuclease to form a nucleotide which is treated with nucleotidase or alkaline-phosphatase to generate nucleoside, or for assaying its substrate RNA or DNA; a sample for assaying the activity of nucleotidase in which a nucleotide such as AMP is hydrolyzed by nucleotidase to liberate a nucleoside, or for assaying its substrate AMP; a sample for assaying the activity of an enzyme which liberates nucleoside, for example adenosine formation by S-adenosyl-L-homocysteine hydrolase or guanosine or deoxyguanosine formation by guanosine phosphorylase, or for assaying its substrate; a sample for assaying the activity of enzymes which decompose a nucleoside as a substrate, for example, the hydrolysis of nucleoside by nucleosidase, the hydrolysis of inosine by inosinase, the hydrolysis of uridine by uridinenucleosidase, the decomposition of uridine by uridinephosphorylase, or the decomposition of thymidine by thymidinephosphorylase; a sample for assaying an enzyme with a phosphorylated 5'-hydroxy group of a nucleoside as the substate, for example the phosphorylation of the 5'-hydroxy group of adenosine by adenosine kinase, the phosphorylation of the 5'-hydroxy group of uridine by uridinekinase or the phosphorylation of the 5'-hydroxy group of thymidine by thymidinekinase; and a sample for the quantitative assay of purine nucleoside in a reaction system of nucleoside phosphorylase or the enzymatic activity of purine nucleoside phosphorylase.

The incubation temperature for these samples and nucleoside oxidase is generally 37° C., and the incubation time need not be limited. The reaction proceeds according to the reaction schemata of [II], [III], [IV], [V], [VI] and/or [VII] or [VIII], [IX] and/or [X] hereinbefore, and the amount of consumed oxygen or generated hydrogen peroxide is measured for quantitative analysis. Oxygen is preferably measured by an oxygen electrode and hydrogen peroxide is determined by electrical means such as a hydrogen peroxide electrode or by chemical means, for example, using conventional known reagents for the quantitative determination of hydrogen peroxide, such as a combination of phenol, 4-aminoantipyrine and peroxidase, or a combination of phenol, 4-aminophenazole and peroxidase, or a combination of N,N'-diethyl-m-toluidine, 4-aminoantipyrine and peroxidase.

Thus the amount of nucleoside in the sample can be determined according to phenomenon of consumption of two moles of oxygen or two moles of hydrogen peroxide per mole of nucleoside.

One embodiment of assay for nucleosides in a sample, is that the aliquot sample dissolved in a buffer is added in a solution of nucleoside oxidase 1–20 U., incubated at 37° C., and consumed oxygen is measured by a oxygen electrode or generated hydrogen peroxide is determined by a hydrogen peroxide electrode. Also, generated hydrogen peroxide can be determined by adding N,N-diethyl-m-toluidine, 4-aminoantipyrine and peroxidase and the mixture is incubated at 37° C., then colorimetrically measured at 545 nm. Another embodiment of assay for enzymatic activity is that after enzymatic reaction for suitable time, the consumed nucleoside or produced nucleoside is assayed by the procedures hereinbefore explained. Adenosine kinase can be assayed by measuring the amount of consumed adenosine after incubating the mixture of adenosine kinase, ATP and adenosine. Nucleotidase can be assayed by measuring the amount of consumed oxygen or generated hydrogen peroxide in the reaction with nucleoside oxidase and adenosine which is formed by enzymatic action on a substrate ATP. For RNA content or ribonuclease activity in a sample, RNA is reacted with ribonuclease to form a nucleotide which is converted to a nucleoside by an action of nucleotidase or alkalinephosphatase, then the said nucleoside is quantitatively measured by nucleoside oxidase thereby assaying RNA content or ribonuclease activity.

As hereinabove explained, the novel enzyme nucleoside oxidase can be advantageously used for the quantitative analysis of various nucleosides, or to assay for enzymatic activity on nucleosides as substrates, or for assays for enzymatic activity which forms nucleosides or substrates thereof.

The following examples illustrate the present invention but are not to be construed as limiting:

EXAMPLE 1

Into an aqueous medium (100 ml, pH 7.0) comprising peptone 1.0 w/w%, casein 1.0 w/w%, oleic acid 1.0 w/w%, yeast extract powder 0.5 w/w%, KCl 0.2 w.w%, $K_2HPO_4$ 0.1 w/w%, $MgSO_4.7H_2O$ 0.05 w/w%, sterilized at 120° C. for 20 minutes, in an Erlenmeyer flask, was inoculated *Pseudomonas putida* B-0781 FERM-P No. 5664 and the mixture was cultured at 30° C. for 1 day. This seed culture was inoculated into the same medium hereinabove [20 l. containing Desfoam BC-51Y (trade name) 0.1%] in a 30 l. jar-fermenter and was cultured with sterilized aeration at 30° C. for 42 hours at 350 r.p.m., with aeration 20 l./min.

The cultured cells were collected centrifugally at 5000 r.p.m. for 10 minutes. The collected cells were washed with water (7 l.) and again collected under the same conditions as hereinabove. To the cells suspended in 20 mM phosphate buffer (pH 7.0, 5 l.) containing 10 mM EDTA was added lysozyme (final lysozyme concentration: 0.5 mg/ml) and the mixture was stirred at 37° C. for 5 hours for cell destruction. The supernatant (4.2 l., 2.86 U./ml) was removed by centrifugation at 5000 r.p.m. for 10 minutes. Cold acetone (−20° C., 2.5 l.) was added to the supernatant and the mixture was sedimented centrifugally at 5000 r.p.m. for 10 minutes to separate the supernatant (11150 U.) Further cold acetone (2.5 l.) was added to the supernatant, and the mixture was centrifuged at 5000 r.p.m. for 10 minutes to obtain the sedimented material. The precipitate was dissolved in 20 mM phosphate buffer (pH 7.0, 1.0 l.) and centrifuged at 5000 r.p.m. for 15 minutes to separate the insolubles. The supernatant (9700 U.) was treated at 50° C. for 20 minutes and the heat denatured protein was separated by centrifugation at 5000 r.p.m. for 10 minutes to obtain the supernatant (9400 U.) Ammonium sulfate (319 g) was added to the supernatant solution up to 0.42 saturation and the mixture was centrifuged at 15,000 r.p.m. for 10 minutes to separate the precipitate, then ammonium sulfate (140 g) was added to obtain the precipitate. The precipitate, dissolved in 20 mM phosphate buffer (pH 7.5, 50 ml), was centrifuged at 15,000 r.p.m. for 10 minutes to separate the insolubles. The supernatant solution (7800 U.) was dialyzed in a cellophane tube against 20 mM phosphate buffer overnight. The dialyzed solution was charged on a column (2.6×60 cm) of DEAE-cellulose (product of Selver Co.) equilibrated with 20 mM Tris-HCl buffer (pH 7.5) and eluted with a linear gradient of 0–0.5 M KCl in 20 mM Tris-HCl buffer (pH 7.5) to collect the eluted fraction at 0.15–0.25 M KCl concentration (5760 U.) which was concentrated by an Amicon PM-10 membrane (trade name). The latter concentrate was charged on a column (2.6×90 cm) of Sephacryl S-200 (product of Pharmacia Co.) Active fractions checked at 280 nm absorption with enzyme activity were collected and lyophilized to obtain the purified nucleoside oxidase powder (51.0 mg, 3675 U.)

EXAMPLE 2

A mixture of adenosine (500 mg), nucleoside oxidase (180 U.), catalase (15,000 U.) and distilled water (90 ml) is added to a 0.2 M dimethylglutarate-NaOH buffer (pH 6.0, 10 ml) and incubated with stirring at 150 r.p.m., aeration at 20 ml/min. at 37° C. for 90 minutes. The pH was adjusted to control the pH of the incubation mixture. After incubation, the pH was adjusted to pH 2.0 by adding 0.1 N HCl to sedimentate the materials. The precipitate was collected by centrifugation (15,000 r.p.m., 10 minutes), washed with aqueous HCl (pH 3), dissolved in 1 N NaOH and again precipitated by adjusting to pH 3 by adding HCl to collect crystals (465 mg). The product was identified with authentic adenosine-5'-carboxylic acid by elemental analysis, molecular weight, IR-spectrum, UV-spectrum and thin layer chromatography.

EXAMPLE 3

In Example 2, adenosine was replaced by guanosine, thymidine, cytidine, inosine, xanthosine, uridine, arabinosylcytosine, arabinocyladenine, 2'-deoxyadenosine and 2'-deoxyguanosine (each 300 mg) to obtain 5'-carboxylic acid as follows:

| Substrate | Product |
|---|---|
| guanosine | guanosine-5'-carboxylic acid (268 mg) |
| thymidine | thymidine-5'-carboxylic acid (245 mg) |
| inosine | inosine-5'-carboxylic acid (254 mg) |
| xanthosine | xanthosine-5'-carboxylic acid (265 mg) |
| uridine | uridine-5'-carboxylic acid (258 mg) |
| arabinosylcytosine | arabinosylcytosine-5'-carboxylic acid (220 mg) |
| arabinosyladenine | arabinosyladenine-5'-carboxylic acid (267 mg) |
| 2'-deoxyadenosine | 2'-deoxyadenosine-5'-carboxylic acid (270 mg) |
| 2'-deoxyguanosine | 2'-deoxyguanosine-5'-carboxylic acid (266 mg) |

EXAMPLE 4

A mixture (0.95 ml) consisting of the following was pre-incubated at 37° C.:

| | |
|---|---|
| 0.2 M dimethylglutarate-NaOH buffer (pH 6.0) | 0.4 ml |
| 0.2 w/w % N,N—diethyl-m-toluidine | 0.1 ml |
| 0.3 w/w % 4-aminoantipyrine | 0.1 ml |
| peroxidase (50 U./ml) | 0.1 ml |
| nucleoside oxidase | 10 U. |
| distilled water | 0.25 ml |
| Total | 0.95 ml |

Figure 6:
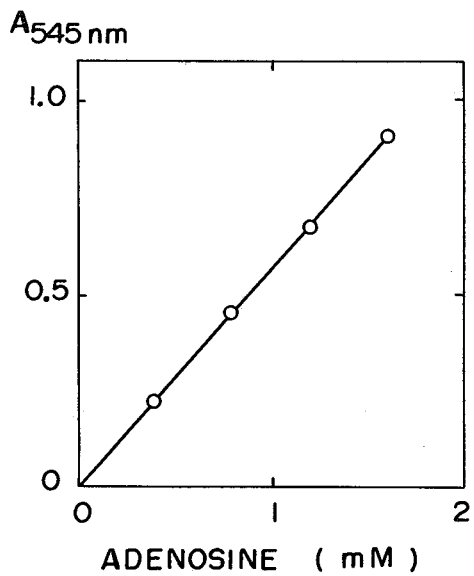
FIG. 6 is a graph of the colorimetric analysis of adenosine in a mixture incubated with nucleoside oxidase according to the present invention.

To that solution was added various concentrations of adenosine solution (0.05 ml) and distilled water (2.0 ml) and the resultant solutions were colorimetrically measured at 545 nm. As shown in FIG. 6, the adenosine content was analyzed with good accuracy.

EXAMPLE 5

Figure 7:
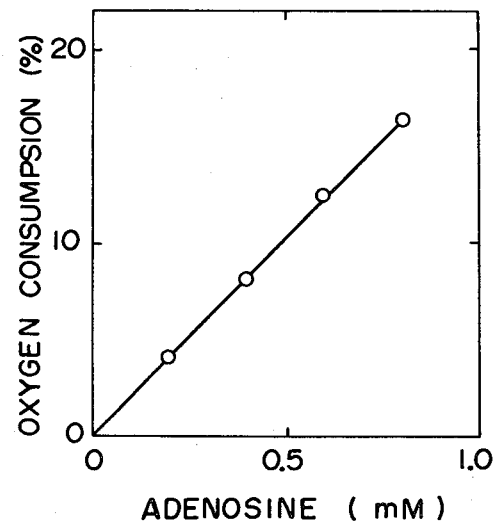
FIG. 7 is a graph similar to FIG. 6, but in which analysis is performed by the measurement of oxygen consumption.

A mixture (0.95 ml) the same as in Example 4 was pre-incubated at 37° C. Various concentrations of adenosine sample solution (0.05 ml) were added, and the resultant solutions were incubated at 37° C. for 20 minutes and the consumed oxygen was measured with an oxygen electrode (product of Ishikawa Mfg. Co.) As shown in FIG. 7, the results were good as to the accuracy of the quantitative analysis of adenosine.

EXAMPLES 6–12

The adenosine solution of Example 4 was replaced by various concentration of guanosine, thymidine, inosine, uridine, 2'-deoxyadenosine, arabinosyladenine or bredinine (4-carbamoyl-1-β-D-ribofuranosyl-imidazolium-5-oleate), and the reaction conditions were the same as those of Examples 4 and 5.

Figure 8:
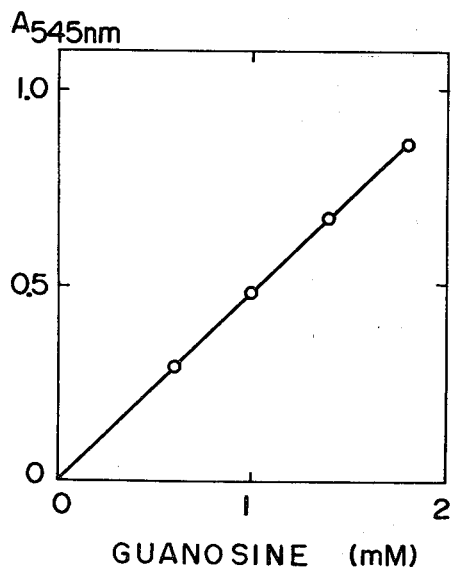
FIGS. 8–13 are graphs similar to FIG. 6, but show the quantitative analysis for various other nucleosides.
Figure 9:
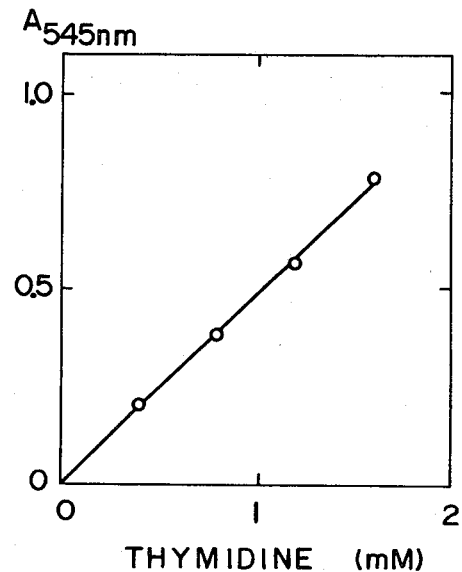
Figure 10:
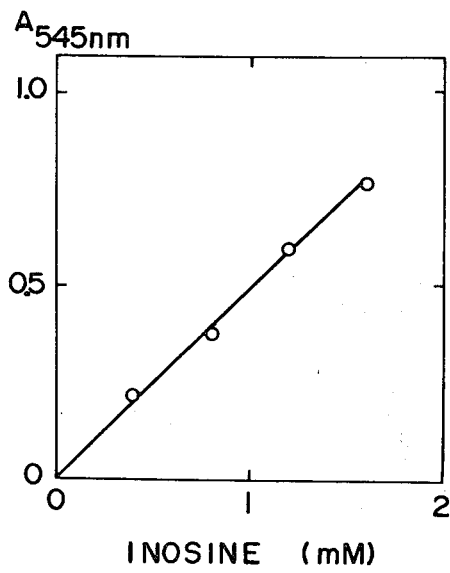
Figure 11:
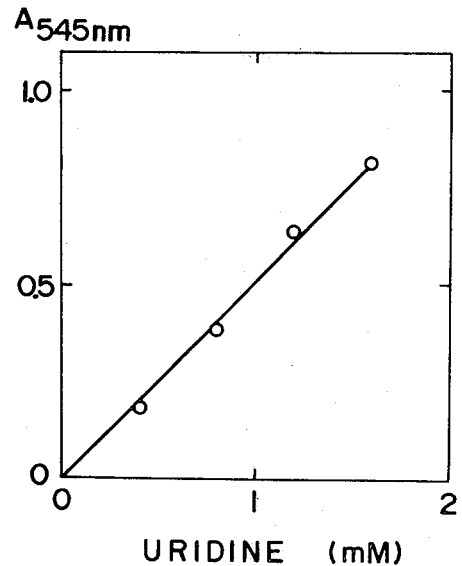
Figure 12:
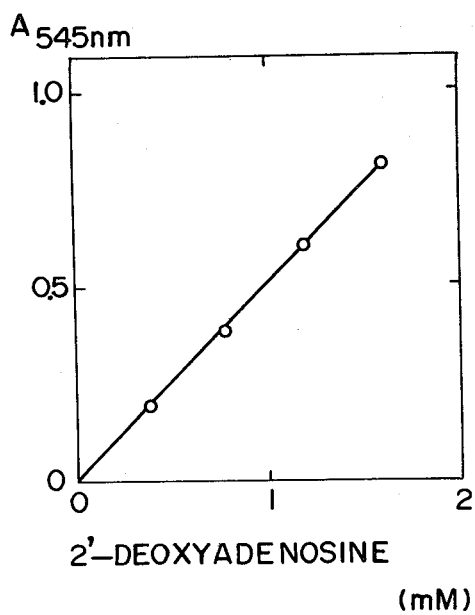
Figure 13:
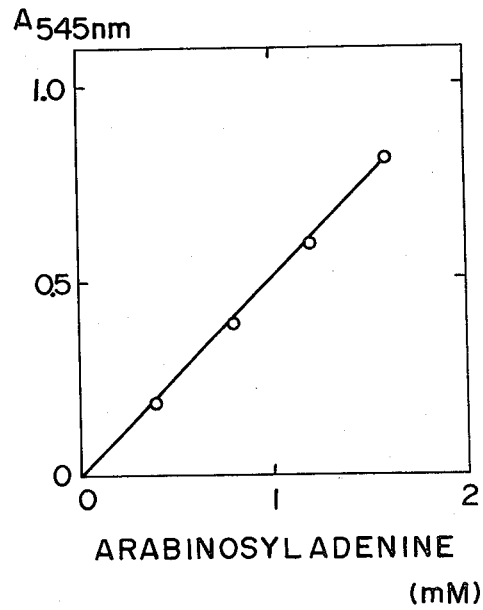
Figure 14:
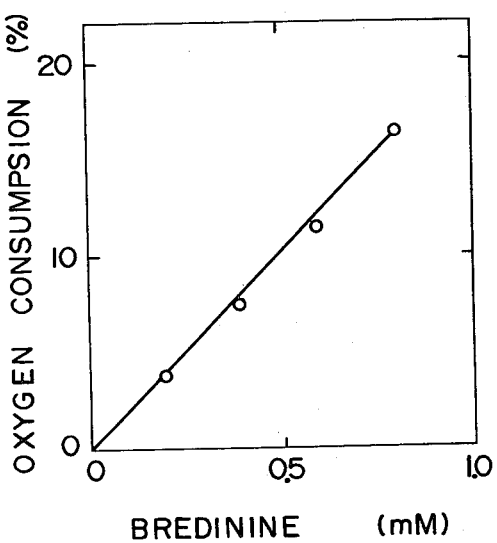
FIG. 14 is a graph similar to FIG. 7, but for the quantitative determination of bredinine.

The results are shown in FIG. 8 (guanosine), FIG. 9 (thymidine), FIG. 10 (inosine), FIG. 11 (uridine), FIG. 12 (2'deoxyadenosine), FIG. 13 (arabinosyladenine) and FIG. 14 (bredinine (oxygen electrode method)) and manifest good accuracy.

EXAMPLE 13

| | |
|---|---|
| 0.2 M dimethylglutarate-NaOH buffer (pH 6.0) | 0.4 ml |
| 0.2 w/w % N,N—diethyl-m-toluidine | 0.1 ml |
| 0.3 w/w % 4-aminoantipyrine | 0.1 ml |
| peroxidase (50 U./ml) | 0.1 ml |
| nucleoside oxidase | 5 U. |
| distilled water | 0.25 ml |
| Total | 0.95 ml |

Figure 15:
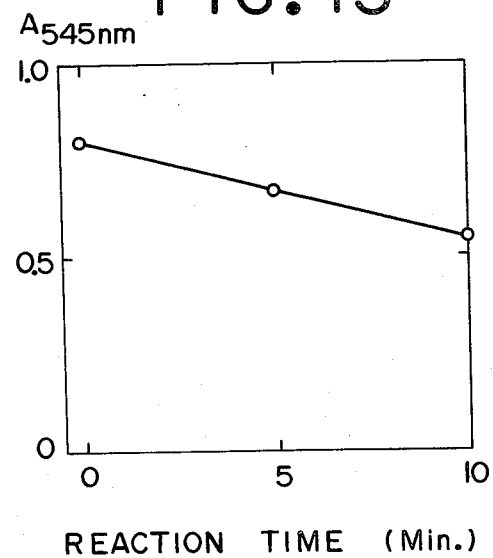
FIG. 15 is a graph of the effect of reaction time on colorimetric analysis in the case of adenosine kinase.

A mixture consisting of the above was prepared. Adenosine kinase solution (0.1 ml) prepared by the method in J. Biol. Che., 193, 481–495 (1951) was added in 0.2 M dimethylglutarate-NaOH buffer (pH 6.0) (containing ATP 5 mM, adenosine 5 mM and $MgCl_2$ 10 mM) (0.4 ml) and the mixture was incubated at 37° C. At 0 minute, 5 minutes and 10 minutes, portions of the reaction mixture (0.02 ml) were collected, heated at 70° C. and added to the above reaction mixture, which was incubated at 37° C. for 20 minutes, and colorimetrically measured at 545 nm. The results are shown in FIG. 15.

EXAMPLE 14

| | |
|---|---|
| 0.2 M dimethylglutarate-NaOH buffer (pH 6.0) | 0.4 ml |
| 0.2 w/w % N,N—diethyl-m-toluidine | 0.1 ml |
| 0.3 w/w % 4-aminoantipyrine | 0.1 ml |
| peroxidase (50 U./ml) | 0.1 ml |
| 20 mM AMP | 0.05 ml |
| nucleoside oxidase | 10 U. |
| distilled water | 0.2 ml |
| Total | 0.95 ml |

The reaction mixture (0.95 ml) of the above was pre-incubated at 37° C. Nucleotidase solution (product of Sigma Co.) (0.05 ml) was added thereto, and the mixture was incubated at 37° C. for 20 minutes and colorimetrically measured at 545 nm.

Figure 16:
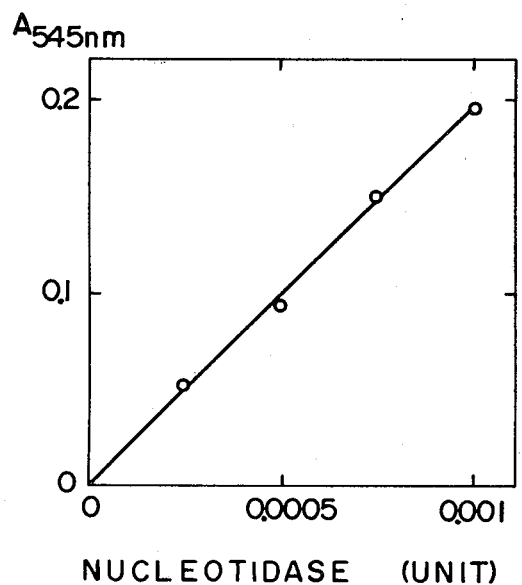
FIGS. 16 and 17 are views similar to FIG. 6, but for the colorimetric analysis of nucleotidase and ribonuclease, respectively.

The results are shown in FIG. 16. Nucleotidase was quantitatively analyzed with good accuracy.

EXAMPLE 15

A reaction mixture (0.95 ml) containing RNA and nucleotidase was incubated with ribonuclease solution (0.05 ml) at 37° C. for 30 minutes. 0.05 ml thereof heated at 80° C. was added to a reaction mixture (0.95 ml) which was the same as in Example 4. This reaction mixture was then incubated at 37° C. for 20 minutes, and colorimetrically measured at 545 nm.

Figure 17:
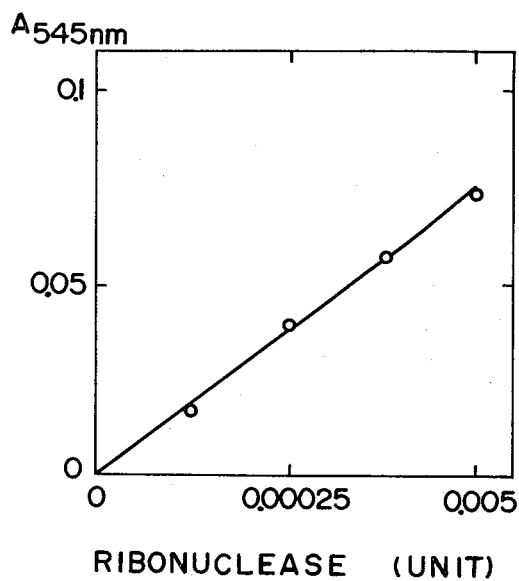

The results are shown in FIG. 17. Ribonuclease can be analyzed with good accuracy.

What is claimed is:

1. Nucleoside oxidase having the following substrate specificity and enzymatic action:

substrate specificity on a nucleoside of the formula [I]

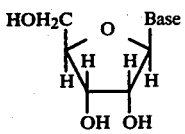

wherein Base means nucleic acid base residue, enzymatic action to catalyze at least one enzymatic reaction of the formulae [II] and [III]

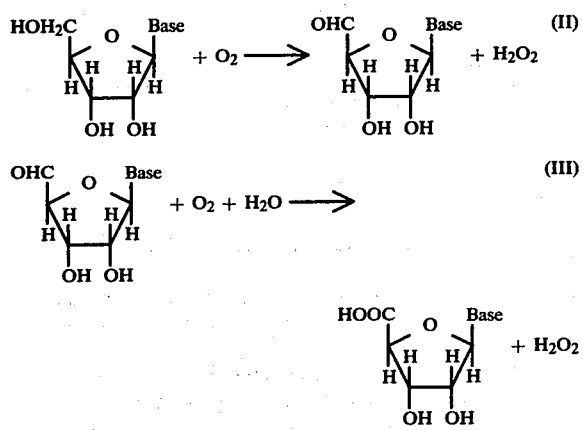

2. Nucleoside oxidase as claimed in claim 1, having the following values:
   Km value: $4.5 \times 10^{-5}$ (for adenosine),
   isoelectric point: about pH 4.7 (electrophoresis using carrier ampholite),
   molecular weight: about 240,000,
   optimum pH: pH 5-6,
   optimum temperature: 45°-55° C.,
   heat stability: stable below 60° C. for 10 minutes,
   pH stability: stable up to pH 8-9.

3. A process for the production of nucleoside oxidase which comprises culturing a nucleoside-oxidase-producing microorganism belonging to the genus Pseudomonas in a nutrient medium containing an assimilable carbon source, assimilable nitrogen source and inorganic salt, and isolating the thus-formed nucleoside oxidase from the cultured cells.

4. A process as claimed in claim 3, wherein the said nucleoside-oxidase-producing microorganism is *Pseudomonas putida* B-0781 FERM-P No. 5664.

5. A process for the production of a nucleoside-5'-carboxylic acid, which comprises incubating nucleoside oxidase with a nucleoside having a 5'-hydroxymethyl group, in an aqueous medium under aerobic conditions, and isolating the thus-formed nucleoside-5'-carboxylic acid from the incubation medium.

6. A process as claimed in claim 5, wherein the said nucleoside having a 5' -hydroxymethyl group is selected from the group consisting of adenosine, guanosine, thymidine, cytidine, inosine, xanthosine, uridine, arabinosylcytosine, arabinosyladenine, 2'-deoxyadenosine and 2'-deoxyguanosine.

7. An assay method for a nucleoside in a liquid sample, which comprises incubating the said sample with nucleoside oxidase, which consumes oxygen and generates hydrogen peroxide and nucleoside-5'-carboxylic acid by acting on nucleoside, and quantitatively determining consumed oxygen or generated hydrogen peroxide.

8. An assay method claimed in claim 7, wherein the said nucleoside oxidase has the following properties:

substrate specificity on a nucleoside of the formula [I]

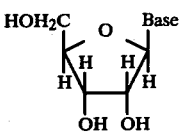

wherein Base means nucleic acid base residue, enzymatic action to catalyze at least one enzymatic reaction of the formulae [II] and [III]

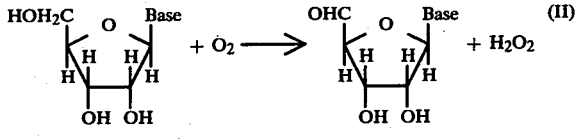

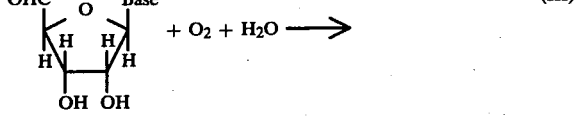

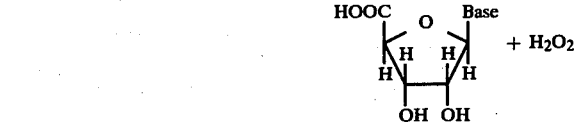

9. An assay method as claimed in claim 7, wherein the said liquid sample contains a nucleoside or a nucleoside-generating system.

10. An assay method as claimed in claim 9, wherein the said liquid sample containing a nucleoside-generating system contains at least a nucleoside liberated by the action of a nucleotidase on a nucleotide.

11. An assay method as claimed in claim 9, wherein the said liquid sample containing a nucleoside-generating system contains at least a nucleoside liberated by the action of ribonuclease or deoxyribonuclease and a nucleotidase or a phosphatase.

12. A kit for nucleoside assay, which comprises at least nucleoside oxidase which consumes oxygen and generates hydrogen peroxide and nucleoside-5'-carboxylic acid by acting on a nucleoside.

13. A kit claimed in claim 12, wherein the said kit contains at least nucleoside oxidase and a reagent for measuring the amount of generated hydrogen peroxide.

14. A kit claimed in claim 13, wherein the said reagent for measuring an amount of generated hydrogen peroxide is a composition for reacting with hydrogen peroxide and converting a reaction product to a detectable substance.

15. A kit claimed in claim 14, wherein the said composition is a chromogen which contains at least peroxidase.

* * * * *